United States Patent [19]
Zaffaroni et al.

[11] 4,273,872
[45] Jun. 16, 1981

[54] METHOD FOR THE MICROBIOLOGICAL CONVERSION OF STEROIDS

[75] Inventors: Pasquale Zaffaroni, Mentana; Vincenza Vitobello; Anna M. Gamalerio, both of Rome, all of Italy

[73] Assignee: Snamprogetti S.p.A., Milan, Italy

[21] Appl. No.: 93,913

[22] Filed: Nov. 13, 1979

Related U.S. Application Data

[63] Continuation of Ser. No. 926,232, Jul. 20, 1978, abandoned, which is a continuation of Ser. No. 797,877, May 17, 1977, abandoned.

[30] Foreign Application Priority Data

May 18, 1976 [IT] Italy ............................. 23359 A/76

[51] Int. Cl.³ ............................................. C12P 33/16
[52] U.S. Cl. .................................... 435/55; 435/249; 435/822
[58] Field of Search ........................................ 435/55

[56] References Cited

U.S. PATENT DOCUMENTS

| | | | |
|---|---|---|---|
| 2,697,062 | 12/1954 | Cramer | 435/55 |
| 3,222,258 | 12/1965 | Iizuka et al. | 435/248 |
| 3,308,035 | 3/1967 | Douvas | 435/248 |
| 3,355,296 | 11/1967 | Perkins et al. | 435/249 |
| 3,684,656 | 8/1972 | Waard | 435/55 |
| 3,684,657 | 8/1972 | Kraychy et al. | 435/55 |

*Primary Examiner*—Alvin E. Tanenholtz
*Attorney, Agent, or Firm*—Morgan, Finnegan, Pine, Foley & Lee

[57] ABSTRACT

A method is disclosed for the microbiological transformation of steroids, especially cholesterol, by employing culture media which contain hydrocarbons rather than carbohydrates. Paraffinic hydrocarbons, particularly normal paraffins from 15 to 20 carbon atoms, are used as the only carbon and energy sources. SP2T (NRRL B-11, 112), SP3T bis (NRRL B-11, 113), SP5T (NRRL B-11, 114), SP7T/1 (NRRL B-11, 115), SP742XXA (NRRL B-11, 116), SP731RD (NRRL B-11, 117), and SP734D (NRRL B-11, 118) are bacterial strains which can be used to this purpose.

8 Claims, No Drawings

METHOD FOR THE MICROBIOLOGICAL CONVERSION OF STEROIDS

This is a continuation of application Ser. No. 926,232, filed July 20, 1978, now abandoned.

This invention relates to a novel method for the microbiological modification of steroids, which is based on their co-oxidation with hydrocarbons.

The microbiological conversions of steroids are exploited long since for the production of derivatives having particular pharmacological activities or for the preparation of intermediates useful in the production of such derivatives (W. Charney and W. L. Herzog-Microbial Transformations of Steroids Handbook - Academic Press, New York 1967).

These transformations are normally performed by cultivating appropriate cultural microbial strains which contain carbohydrates and/or other complex substrates as a source of carbon and of energy.

Under these conditions the microbiological transformations of the steroidal substrates have no direct relationship with the metabolism of the microbial strains which perform them and it seems that they could rather be attributed to detoxification mechanisms (A. Capek, O. Hane and M. Tadra—Microbial Transformations of Steroids—Academia, Prague 1966 pp. 63–64).

We have now found that the microbiological transformations on steroids of preminent industrial importance (hydroxylation, dehydrogenation, side chain demolition) can be encouraged by using hydrocarbons rather than carbohydrates in the culture media.

The microbial strains used in the practice of the present invention had been isolated from samples of different origin (soil, sewage waters) usually drawn in the neighbourhood of refineries or of petrochemical installations.

These samples were used for inoculating enrichment cultures containing mixtures of hydrocarbons as the only source of carbon and energy. The strains were purified according to the conventional microbiological procedures. The isolated strains were maintained on PS agar slants (TABLE I).

TABLE I

Composition of the culture media (grams per liter)

| Medium | PS (maintenance) | AM3 (preculture) | M9-YE (culture) |
|---|---|---|---|
| Peptone | 6 | 5 | — |
| Yeast autolysate | 3 | — | — |
| Casein hydrolysate | 4 | — | — |
| Meat extract | 1,5 | 1,5 | — |
| Yeast extract | — | 1,5 | 0,1 |
| Glucose | — | 1 | — |
| NaCl | — | 3,5 | 0,5 |
| NH$_4$Cl | — | — | 1 |
| MgSO$_4$ . 7 H$_2$O | — | — | 0,2 |
| KH$_2$PO$_4$ | — | 1,32 | 3 |
| K$_2$HPO$_4$ | — | 3,68 | — |
| Na$_2$HPO$_4$ . 12 H$_2$O | — | — | 6 |
| Agar | 25 | — | — |
| pH | 7,3 | 7 | 6,9 |

The source of carbon in the M9-YE medium is specified in the Examples.

For performing the method which is the subject matter of the present invention, from the slant there were inoculated cultures of AM3 medium (TABLE I) and with these precultures were inoculated cultures of minimum culture M9-YE (TABLE I) containing a mixture of nor.paraffins $C_{15}$–$C_{20}$ as a single source of carbon and energy.

The composition of the paraffin mixture is reported in TABLE II.

TABLE II

| Characteristics of the nor . paraffin mixture . — | |
|---|---|
| $D_{15/4°}$ C. | 0.7470 |
| nor . paraffins (% by wt.) | 99.40 |
| nor . $C_{13}$ | 1.0 |
| nor . $C_{14}$ | 3.4 |
| nor . $C_{15}$ | 9.7 |
| nor . $C_{16}$ | 16.2 |
| nor . $C_{17}$ | 19.1 |
| nor . $C_{18}$ | 17.3 |
| nor . $C_{19}$ | 14.7 |
| nor . $C_{20}$ | 11.3 |
| nor . $C_{21}$ | 5.2 |
| nor . $C_{22}$ | 1.2 |
| nor . $C_{23}$ | 0.3 |
| iso- and cyclo-parraffins | 0.40 |
| aromatics | 0.20 |

When the cultures showed a satisfactory growth, they were supplemented with the steroidal substances to be transformed in suspension, in water or in the mixture of nor.paraffins, micronized with supersonic vibrations, or as a solution in an organic solvent (ethanol, acetone, dimethylformamide).

After an appropriate period of time, the cultures were extracted with a solvent immiscible with water, such as chloroform or ethyl acetate.

The extracts were evaporated and examined by thin-layer chromatography (TLC) and/or gaschromatographically.

The structure of the steroid modification products was attributed by comparison of the chromatographic properties (TLC and gas-chromatography) with those of an original sample and/or by infrared spectrometry, mass spectrometry; nuclear magnetic resonance.

In order to establish that the observed transformations were actually caused or exalted by the use of hydrocarbons as the single source of carbon of energy, cultures were raised in parallel, in which the carbon source was formed, respectively, by glucose, a mixture of nor. paraffins with the steroid without any other carbon source.

We have found that, actually, by adding steroids to cultures of a few strains which use hydrocarbons as carbon source and energy source, transformation products are obtained which are not obtained or which are obtained with much lower yields when the same strains are cultured in the presence of glucose and the steroid only as a source of carbon and of energy. We have also observed that by varying a few physico-chemical parameters (temperature, pH, presence of certain ions) it is possible to modify qualitatively and/or quantitatively, the products of transformation of the steroids added to the microbial cultures.

By using the method which is the subject-matter of the present invention, it is possible to carry out very selective oxidations with very high yields, such as the oxidation of cholesterol to -cholestene-3-one, thus obtaining from cheap sources more appreciable products (production of $\Delta^{1,4}$-androstadiene-3,17-dione from cholesterol, production of $\Delta^4$-androstene-3,17-dione and $\Delta^{1,4}$-androstadiene-3,17-dione from progesterone.

The reactions which have been observed under conditions of co-oxidation with hydrocarbons are:

demolition of the steroid side-chain such as in cholesterol or progesterone, to 17-ketosteroids;

oxidation of the —OH froup in the 3-position of several steroids to a group =CO in the 3-position;

$\Delta^1$-dehydrogenation of several steroids.

Among the side reaction there have been observed:

reduction of the =CO group in the 3-position to an OH group in the 3-position;

reduction of the —O—CO group in the 2-position to the O—OH group in the 2-position;

reduction of the double bond between the carbon atoms in the 4 and 5 positions.

It should be noted that with such a method of co-oxidation the demolition of the side chains takes place without the demolition of the steroidal core to a considerable degree.

This invention is illustrated but not limited by the following Examples.

EXAMPLE 1

Effect of the Carbon Source on the Selectivity of the Oxidation of Cholesterol to $\Delta^4$-cholestene-3-one.

A slant of the bacterial strains SP2T (NRRL B-11, 112), SP3T bis (NRRL B-11, 113), SP5T (NRRL B-11, 114) and SP 7T/1 (NRRL B-11,115) having an age of 48 hours was washed with 6 mls of sterile water. With 2 mls of the suspension a 500-ml Erlenmeyer flask containing 100 mls of the AM3 medium was inoculated.

The preculture flasks were incubated during 24 hours at 30° C. on a rotary stirrer (200 rpm, 3.5 cm displacement).

With 2 mls of the preculture other flasks of the minimum medium M9-YE which contained, respectively, 1% volume/volume of $C_{15}$-$C_{20}$ nor.paraffins, 1% weight/volume of glucose and 0.1% weight/volume of cholesterol, in the form of a micronized aqueous slurry.

After a 40-hour incubation under the same conditions of the pre-cultures, to the flasks containing nor.paraffins or glucose were added 100 milligrams/100 of cholesterol, as a micronized slurry in a mixture of nor.paraffins or $H_2O$.

After 40 hours of incubation the cultures were extracted with ethyl acetate: the extracts, dried over anhydrous $Na_2SO_4$ were evaporated to dryness and made up to a final volume of 2 mls with absolute ethanol.

These solutions of the extracts were analyzed by thin layer chromatography: the plates were first eluted with pentane and then with a mixture formed by chloroform and ethyl ether 80/20 volume/volume.

After the second elution the plates were sprayed with a mixture of concentrated $H_2SO_4$ and ethanol, 1/1 (volume/volume) and heated for 8 minutes at 110° C.

On the plates, together with the residue of cholesterol ($R_F=0.37$ violet spots) there appeared a more or less marked spot of a golden-yellow color with an $R_F=0.61$.

By preparatory chromatography the compound having the $R_F=0.61$ was isolated and purified, crystallized from methanol and identified, on the basis of the infrared spectrum and the mass spectrum as $\Delta$4-cholostene-3-one.

For the quantitative determination of the oxidation product, the extracts of the cultures were analyzed by gas-chromatography using a column of XE-60 3% on Chromosorb 80-10 mesh.

The results of the gas-chromatographical analysis are reported in TABLE III.

TABLE III
SELECTIVITY OF THE CO-OXIDATION OF CHOLESTEROL WITH NOR . PARAFFINS .—

| STRAIN | Carbon source | Cholesterol mg/100 mls | $\Delta^4$-Cholestene-3-One mg/100 mls. |
|---|---|---|---|
| 2T | Cholesterol | 58.8 | 36.3 |
|  | nor . paraffins + cholesterol | 5.2 | 89.8 |
|  | glucose + cholesterol | 58.1 | 36.9 |
| 3T bis | Cholesterol | 56.6 | 38.4 |
|  | nor . paraffins + cholesterol | 3.7 | 91.3 |
|  | glucose + cholesterol | 54.7 | 40.4 |
| 5T | Cholesterol | 64.7 | 30.3 |
|  | nor . paraffins + cholesterol | 4.1 | 90.8 |
|  | glucose + cholesterol | 67.6 | 27.3 |
| 7T/1 | Cholesterol | 58.5 | 36.2 |
|  | nor . paraffins + cholesterol | 1.2 | 93.8 |
|  | glucose + cholesterol | 63.4 | 31.6 |

As can be seen, in the presence of glucose as the carbon source, the quantity of oxidized cholesterol is in the same order of magnitude of that obtained with cholesterol alone, whereas in the presence of hydrocarbons the transformation is almost quantitative.

EXAMPLE 2

Transformation of Cholesterol into $\Delta^{1,4}$-Androstadiene-3,17-Dione

With 2 mls of a preculture of the SP 7T/1 (NRRL B-11, 115) strain obtained as in Example 1 were inoculated Erlenmayer flasks of the volume of 500 mls and containing 100 mls of the minimum medium M9-YE with the 1% volume/volume of the mixture of $C_{15}$-$C_{20}$ nor. paraffins.

After 24 hours of incubation at 30° C. on a rotary stirrer at 220 rpm and with a displacement of 3.5 centimeters, were added in each flask 100 milligrams (mg) of cholesterol as a solution in dimethylformamide.

After 70 hours of additional incubation, the extracts of broth-culture were examined by chromatography on thin layer, as described in Example 1.

In the extracts, in addition to the spot with $R_F=0.61$ (cholestene-3-one) an organ coloured spot appeared, having an $R_F=0.3$.

The product was identified as $\Delta^{1,4}$-androstadiene-3,17-dione (1,4-ADD) by comparison with an original sample.

By gas-chromatographical analysis of the extract, it has been established that the product was present in the broth-culture in the amount of 6.8 milligrams/100 mls, with a yield of 9.23%.

EXAMPLE 3

Effect of the Time of Addition of Cholesterol and the Quantity of Inoculum in the Production of $\Delta^{1,4}$-androstadiene-3,17-dione.

By operating substantially as in Example 2, but adding the cholesterol before the inoculation with the preculture and increasing the inoculum from 2% volume/volume to 5% and to 10%, respectively, the results tabulated in TABLE IV have been obtained.

TABLE IV

EFFECT OF INOCULUM ON THE PRODUCTION OF
$\Delta^{1,4}$-ANDROSTADIENE-3,17-DIONE (1,4-ADD) FROM
CHOLESTEROL

| | Inoculum | | | | | |
|---|---|---|---|---|---|---|
| | 5% steroids (mg/100 ml) | | | 40% steroids (mg/100 ml) | | |
| Time hours | choles- terol | $\Delta^4$- choles- tone | 1,4 ADD | choles- terol | $\Delta^4$- choleste- none | 1,4 ADD |
| 0 | 100 | 0 | 0 | 100 | 0 | 0 |
| 24 | 0 | 75.4 | traces | 0 | 44 | traces |
| 48 | 0 | 61.8 | 6.2 | 0 | 18.8 | 8.4 |
| 72 | 0 | 28.6 | 10.4 | 0 | 18.3 | 13.4 |

As can be seen in the Table, with a 10% inoculum, the yield of $\Delta^{1,4}$-androstadiene-3,17-dione rises to 18.4% of theory.

EXAMPLE 4

Effect of the Carbon Source on the Selectivity of the Microbiological Modifications of Progesterone A test has been conducted such as in Example 1, but using 16 bacterial strains capable of utilizing hydrocarbons as the only carbon source and energy source and adding progesterone instead of cholesterol.

From the examination of the extracts of the broth-cultures by thin layer chromatography, the result was that 7 of the evaluated strains, among which the strains SP 742 XXA (NRRL B-11,116) and 731 RO (NRRL B-11,117), only when they grow at the expenses of the mixture of nor.paraffins, are capable of transforming the progesterone, whereas they do not attack it when they are grown on glucose.

With 4 strains, such as the strain SP 734 D (NRRL B-11,118), progesterone was transformed both in the cultures on glucose and in those on nor-paraffins, but in the latter other products were present which were not formed in the cultures on glucose.

On the chromatograms of the extracts of all the strains there have been observed two principal spots (in addition to those of the residual progesterone). The first spot, of a green colour, having an $R_S$ (progesterone=1) of 0.75, whereas the second, of an organe colour, exhibiting an $R_S=0.50$.

By comparison with original samples, the two products have been identified as $\Delta^4$-androstene-3,17-dione (4-AD) and $\Delta^{1,4}$-androstadiene-3,17-dione (1,4 ADD), respectively.

EXAMPLE 5

Transformation of Progesterone into
$\Delta^4$-androstene-3,17-dione and
$\Delta^{1,4}$-androstadiene-3,17-dione The bacterial strain SP 742 XXA (NRRL B-11,116) is cultured as described in Example 2, but adding to the culturing flasks, after 24 hours as from the inoculation, 100 milligrams of progesterone as a slurry in the mixture of $C_{15}$-$C_{20}$ nor.paraffins.

By gas-chromatographic analysis of the extracts on XE-60 there have been determined quantitatively the products as obtained, as shown in TABLE V.

TABLE V

TRANSFORMATION OF PROGESTERONE WITH THE STRAIN SP 742 XXA

| Time of addition of the progesterone | Steroids in the broth-culture (mg/100 mls) | | |
|---|---|---|---|
| | Progesterone | 4-AD | 1,4-ADD |
| 0 | 100 | — | — |
| 48 | 8.57 | 28.29 | 37.56 |
| 72 | 3.8 | 17.57 | 55.15 |

As can be seen, the maximum yield of 4-AD is 31% at 48 hours, whereas the maximum yield of 1,4-ADD is 61% at 72 hours.

EXAMPLE 6

Co-oxidation of Progesterone in Small Fermentators

On the chromatograms of the extracts of the cultures in the flasks, along with the principal products (4-AD and 1,4-ADD) described in the previous Examples, there could be seen spots of other products which were present in trace quantities.

In order to obtain a greater amount of these products, a co-oxidation test was carried out in small 17-liter fermentators, containing 10 liters of the M9-YE medium to which there had been added 10 mls/liter of the mixture of nor.paraffins.

The fermentators were inoculated with 200 mls of a preculture of the strains SP 742 XXA (NRRL B-11,116), SP 731 RO (NRRL B-11,117) and SP 734 D (NRRL B-11,118). The fermentators were incubated at 30° C. with stirring of 500 rpm and an aeration rate of 5 liters per minute.

After a 24-hour incubation, when the growth of the bacterial strains had been well started, to each fermentator were added 5 grams of solid progesterone, in fine powder and the incubation was carried on for 78 additional hours.

The trend of the co-oxidation of progesterone was followed by sampling the cultures and examining the extracts by thin layer chromatography.

The chromatogram of the samples at 24–78 hours is reported in the chromatograph diagram.

The recovery of the steroids from the broth cultures was carried out as follows:

to the broth cultures there were added 2 liters of ethyl acetate with continuous stirring;

after a few minutes of stirring the motor was stopped and the mixture was allowed to stand;

the supernatant portion was transferred into a separatory funnel to complete the separation of the phases;

the bottom phase was discarded and the top phase dried over anhydrous $Na_2SO_4$;

ethyl acetate was evaporated off in a vacuo;

in the residual nor.paraffins a precipitate was formed, which was recovered by filtration (1st precipitation) and washed with ice-cold nor.pentane, which was added to the filtrate.

CHROMATOGRAPH DIAGRAM

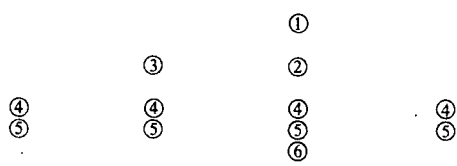

indicate the products of the chromatograph diagram and of TABLE VI).

TABLE VI
PRODUCTS OF THE CO-OXIDATION OF PROGESTERONE

| Spot No. | Color Visible | Color Ultraviolet (F = fluorescent) | Identity | IR (1) | MASS | NMR | 742 XXA | 731 RO | 734 D |
|---|---|---|---|---|---|---|---|---|---|
| 1 | yellow | clear | 5-pregnane-3,20-dione | + | + | | | | + |
| 2 | rose | lilac | | | | | | | + |
| 3 | green | yellow(F) | | | | | | + | |
| 4 | yellow | yellow-green (F) | progesterone | | | | | substrate | |
| 5 | green | yellow(F) | Δ⁴-androstene-3,17-dione | + | | + | + | + | + |
| 6 | brown | clear | Δ¹,⁴-pregnadiene-3,20-dione | + | + | | (2) | (2) | + |
| 7 | orange | orange(F) | Δ¹,⁴-androstadiene-3,17-dione | + | | + | + | + | + |
| 8 | brown | lilac(F) | 5-pregnane-3/3-ol-20-one | + | | | | | + |
| 9 | yellow | yellow(F) | Δ⁴-pregnene-20/3-ol-3-one | + | + | | + | | |
| 10 | green | yellow(F) | testosterone | + | + | | + | + | |
| 11 | yellow | green(F) | | | | | | impurities of substrate | |
| 12 | rose | orange | | | | | + | + | + |
| 13 | rose | orange | | | | | | + | |

NOTES TO TABLE VI:
(1) The infrared spectra were compared with those reported in W. Neudert and H. Ropke - Steroid Spektrenatias - Springer Verlag 1905.
(2) The spot of this product appears in the first hours after the addition of the progesterone, but is then masked by the spot 5.

CHROMATOGRAPH DIAGRAM

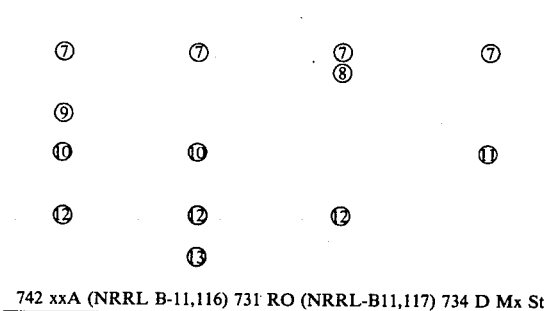

742 xxA (NRRL B-11,116) 731 RO (NRRL-B11,117) 734 D Mx St

To recover the steroid dissolved in the mixture of nor.paraffins and in the nor.pentane, the solution was poured on a column of the diameter of 3 centimeters and charged with 100 grams of silica gel slurried in pentane.

When the entire solution had percolated through the column, the latter was washed with 300 mls of nor.pentane; the percolate contained only the nor.paraffins without any trace of steroids.

The column was then washed with 300 mls of a mixture composed by CHCl₃ (80%) and ethanol (20%).

By evaporation of this second washing liquid there was recovered a second precipitate composed by steroids without any trace of nor.paraffins.

The recovery of the steroids with this method was almost total.

By preparatory thin layer chromatography there have been isolated the major fraction of products which give the spots shown in the chromatograph diagram.

The isolated products were identified by mass spectrometry, infrared spectrometry and by comparison with an original sample.

The results of the identification are reported in TABLE VI.

The products which have been identified are reported in the reaction diagram (the numbers in brackets

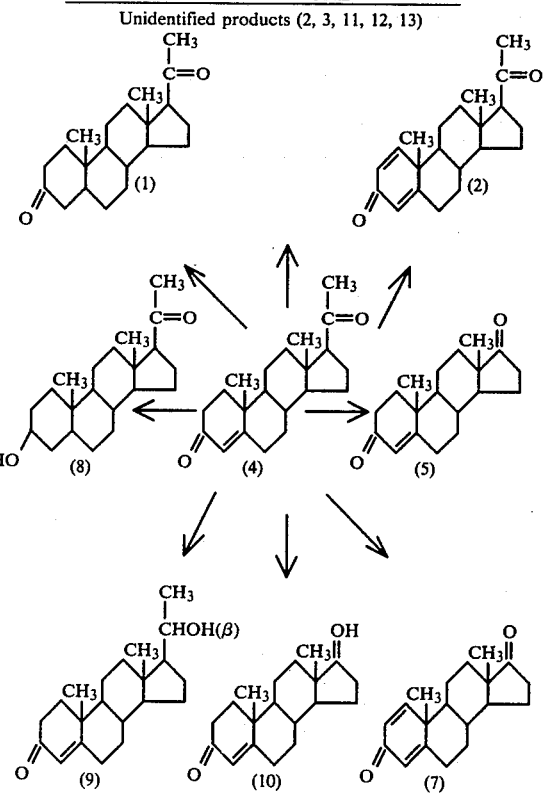

REACTION DIAGRAM
PRODUCTS OF THE CO-OXIDATION OF PROGESTERONE
Unidentified products (2, 3, 11, 12, 13)

It is worth noting the fact that under these conditions of co-oxidation with hydrocarbons also side-reactions take place of reduction to the double bond (1, 8), to the carbonyl in C in the 3 position (8) and to the carbonyl in the C in the 20 position (9).

EXAMPLE 7

EFFECT OF CSL ON THE CO-OXIDATION OF PROGESTERONE

The strains SP 731 RO (NRRL B-11,117) and SP 742 XXA (NRRL B-11,116) were cultured as described in Example 5, with the difference that to the culture medium M9-YE there had been added 5 grams/liter of corn steep liquor (CSL) or liquid in which maize has been soaked.

The trend of the transformations was followed by thin layer chromatography: in no one of the culture was it possible to detect the presence of 4-AD or of 1,4-ADD, but, while in the cultures of the strain SP 731 RO (NRRL B-11,117) there was accumulation of 5-alpha-pregnane-3/3-ol-20-one, in these of the strain 742 XXA (NRRL B-11,116) there was experienced the complete demolition of the progesterone without the accumulation of transformation products.

EXAMPLE 8

EFFECT OF TEMPERATURE ON THE CO-OXIDATION OF PROGESTERONE

The strain SP 742 XXA (NRRL B-11,116) was cultured as described in Example 5, with the difference that the incubation of the flasks was carried out at 25° C. and at 35° C.

The examination of the cultures, by gas-chromatography, has permitted to establish that at 35° C. the demolition of the side chain of the progesterone (P) is inhibited, so that there is the production of $\Delta^1$-progesterone ($\Delta^1$-P) whereas at 25° C. the principal products are the same which had been found at 30° C. that is $\Delta^4$-androstene-3,17-dione (A-AD) and $\Delta^{1,4}$-androstadiene-3,17-dione (1,4-ADD). The results of the gaschromatographic analysis of the broth-cultures are tabulated in TABLE VII.

TABLE VII

| EFFECT OF TEMPERATURE ON THE CO-OXIDATION OF PROGESTERONE | | | | | | | | |
|---|---|---|---|---|---|---|---|---|
| TEMPERATURE | 25° C. | | | | 35° C. | | | |
| hours of addition | steroids (millig./100 mls) | | | | steroids mg/100 mls) | | | |
| of progesterone | P | $\Delta^1$-P | 4-AD | 1,4-ADD | P | $\Delta^1$-P | 4-AD | 1,4-ADD |
| 0 | 100 | — | — | — | 100 | — | — | — |
| 24 | 91.3 | — | 5.8 | 0.85 | 94.6 | 6.3 | — | — |
| 48 | 40.9 | — | 31.3 | 25.8 | 83.3 | 8.6 | — | — |

EXAMPLE 9

EFFECT OF THE $Mn^{++}$ ION ON THE CO-OXIDATION OF PROGESTERONE

The strain SP 742 XXA (NRRL B-11,116) is cultured at 25° C. as in the previous Example, with the difference that a few flasks on the medium M9-YE contained 150 grams liter of $MnSO_4.7 H_2O$.

The examination of the cultures by gaschromatography has permitted to establish that the addition of $Mn^{++}$ stimulates the demolition of the progesterone side chains.

The concentrantions of the steroids in the culture broths which contained $Mn^{++}$ after 24 hours as from the addition of the progesterone were, respectively:

| progesterone | 72.8 | milligrams/100 mls |
| --- | --- | --- |
| 4-AD | 16.2 | " |
| 1,4-ADD | 8.9 | " |

We claim:

1. A method for the mircobiological preparation of $\Delta$-4-cholestene-3-one from cholesterol which comprises adding cholesterol and a mixture of n-parafins to a culture of an organism selected from the group cosisting of SP2T, SP3T bis, SP5T, and SP7T/1; incubating the culture for a sufficient time to produce $\Delta$-4-cholestene-3-one; and thereafter extracting the culture with a water immiscible solvent to obtain $\Delta$-4-cholestern-3-one.

2. A method as defined in claim 1 wherein the organism is SP2T.

3. A method as defined in claim 1 wherein the organism is SP3T bis.

4. A method as defined in claim 1 wherein the organism is SP5T.

5. A method as defined in claim 1 wherein the organism is SP7T/1.

6. A method as defined in claim 1 wherein the n-parafins are $C_{15}$–$C_{20}$ n-parafins.

7. A method for the production of $\Delta$ 1,4-androstadiene-3,17-dione from cholesterol which comprises adding cholesterol and a mixture of n-parafins to a culture of the bacterial strain SP7T/1 incubating the culture for a sufficient period of time to form $\Delta$ 1,4-androstadiene-3,17-dione and thereafter extracting the culture with a water immiscible solvent.

8. A method for the production of $\Delta$ 4-androstene-3,17-dione and $\Delta$ 1,4-androstadiene-3,17-dione from progesterone which comprises adding progesterone and a mixture of n-parafins to a culture of SP 731 RO or SP 742 XXA and incubating the culture for a sufficient time to produce $\Delta$ 4-androstene-3,17-dione and $\Delta$ 1,4-androstadiene-3,17-dione; and thereafter extracting the culture with a water immiscible solvent to obtain $\Delta$ 4-androstene-3,17-dione and $\Delta$ 1,4-androstadiene-3,17-dione.

* * * * *